US00PP26041P2

(12) United States Plant Patent
Smith

(10) Patent No.: US PP26,041 P2
(45) Date of Patent: Nov. 3, 2015

(54) *CHRYSANTHEMUM* PLANT NAMED 'CIFZ0022'

(50) Latin Name: *Chrysanthemum×morifolium*
Varietal Denomination: CIFZ0022

(71) Applicant: SYNGENTA PARTICIPATIONS AG, Basel (CH)

(72) Inventor: Mark A. Smith, Alva, FL (US)

(73) Assignee: Syngenta Participations AG, Basel (CH)

( * ) Notice: Subject to any disclaimer, the term of this patent is extended or adjusted under 35 U.S.C. 154(b) by 76 days.

(21) Appl. No.: 13/999,519

(22) Filed: Mar. 6, 2014

(51) Int. Cl.
*A01H 5/00* (2006.01)

(52) U.S. Cl.
USPC ..... Plt./290

(58) Field of Classification Search
USPC ..... Plt./290
See application file for complete search history.

(56) References Cited

PUBLICATIONS

PLUTO Plant Variety Database Jul. 9, 2015.*

* cited by examiner

*Primary Examiner* — Annette Para
(74) *Attorney, Agent, or Firm* — Joshua L. Price

(57) ABSTRACT

A new garden type *Chrysanthemum* plant named 'CIFZ0022' particularly distinguished by the large sized coral-pink, spoon-tip decorative-type inflorescences, large sized plant with a rounded and mounded habit, and a natural flowering response of early October.

2 Drawing Sheets

Latin name of the genus and species of the plant claimed: *Chrysanthemum ×morifolium.*

Varietal denomination: 'CIFZ0022'.

BACKGROUND OF THE NEW PLANT

The present invention comprises a new *Chrysanthemum*, botanically known as *Chrysanthemum×morifolium*, and hereinafter referred to by the variety name 'CIFZ0022'.

'CIFZ0022' is a product of a planned breeding program. The new cultivar has large sized coral-pink, spoon-tip decorative-type inflorescences, large sized plant with a rounded and mounded habit, and a natural flowering response of early October.

'CIFZ0022' originated from a hybridization made in December 2009 in a greenhouse in Tenjo, Columbia. The female parent was the unpatented, proprietary plant designated 'G0519L1', with purple, duplex-type flower, similar plant habit, but slightly smaller size, and a natural season response that is slower by two weeks when compared to 'CIFZ0022'.

The male parent of 'CIFZ0022' was the unpatented, proprietary plant designated as '06-M030', with light yellow, spider-shape inflorescences, that are somewhat smaller in size, a somewhat smaller overall plant habit, and a natural flowering response one week faster when compared to 'CIFZ0022'.

The resultant seed was sown in October 2010 and grown outdoors in Gilroy, Calif., USA. 'CIFZ0022' was selected as a single flowering plant within the progeny of the stated cross on Feb. 20, 2011 in Gilroy, Calif.

The first act of asexual reproduction of 'CIFZ0022' was accomplished when vegetative cuttings were propagated from the initial selection in April 2011 in a greenhouse in Gilroy, Calif.

BRIEF SUMMARY OF INVENTION

Horticultural examination of plants grown from cuttings of the plant initiated in April 2011, and continuing thereafter, has demonstrated that the combination of characteristics as herein disclosed for 'CIFZ0022' are firmly fixed and are retained through successive generations of asexual reproduction.

'CIFZ0022' has not been observed under all possible environmental conditions. The phenotype may vary significantly with variations in environment such as temperature, light intensity and day length.

A Plant Breeder's Right for this cultivar was applied for in Canada on Mar. 8, 2013 (No. 13-7957). 'CIFZ0022' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0022' with colors being as true as possible with an illustration of this type.

Figure 1:
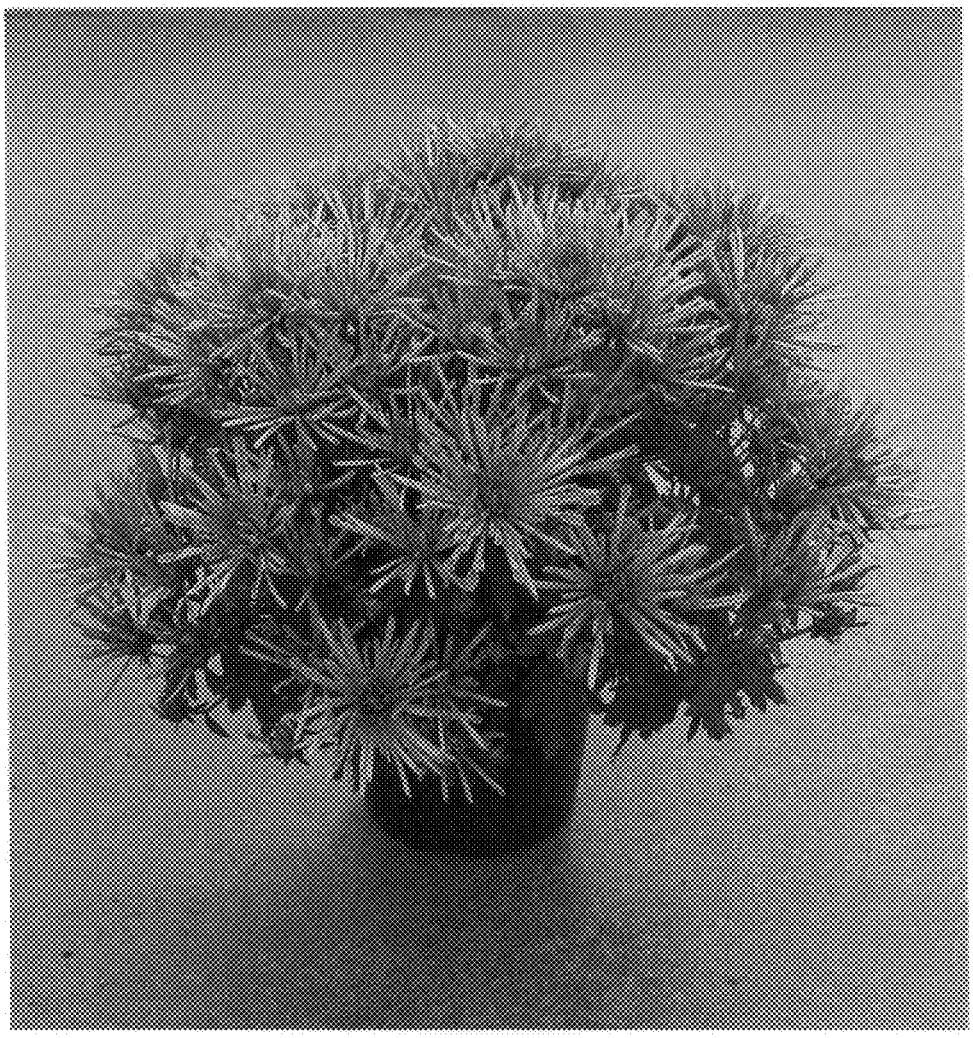
Figure 2:
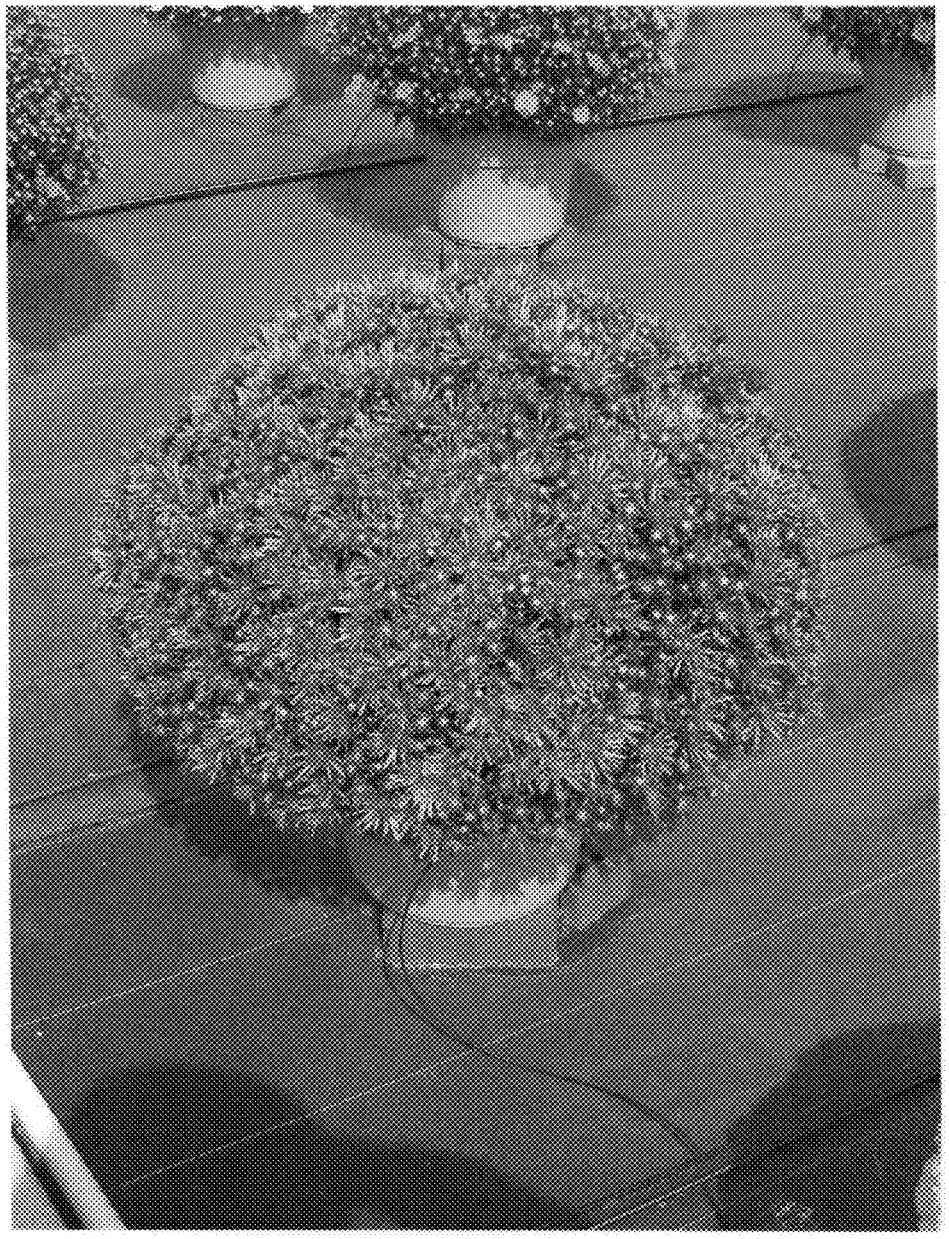

The photographic drawing shows in FIG. 1 a flowering plant of the new variety and in FIG. 2 a flowering plant from an outdoor trial.

DETAILED BOTANICAL DESCRIPTION

The plant descriptions and measurements were taken indoors in Gilroy, Calif. on Feb. 26, 2014 on about 10 week old plants. Rooted cuttings had been planted, 2 plants per pot, in 8 inch pots in week 50, 2013. The plants were not pinched.

The aforementioned photographs: FIG. 1 was taken in Gilroy, Calif. on Aug. 16, 2013, and showing a plant from a trial, in which flowering had been induced by applying black cloth.

FIG. 2 was taken in Monroeville, N.J. on Oct. 3, 2013. These plants were about 12 weeks of age. Three rooted cuttings in a 14 inch pot had been planted in week 28, no pinch. Plants started flowering naturally by early October.

Color references are made to The Royal Horticultural Society Colour Chart (R.H.S.) 2001.

TABLE 1

DIFFERENCES BETWEEN THE NEW VARIETY 'CIFZ0022' AND TWO MOST SIMILAR VARIETIES:

| | 'CIFZ0022' | 'Yolindsay Coral' (U.S. Plant Pat. No. 21,175) |
|---|---|---|
| Flowering response (blackcloth): | ½ week faster | Slower |
| Flowering response (natural): | ½ week faster | Slower |
| Plant size: | Somewhat larger | Somewhat smaller |
| Flower color: | Darker shade of coral | Lighter hue of coral |
| Flower shape: | Spider | Decorative |
| Flower size: | Somewhat larger | Bit smaller |
| Plants, stems, flexibility: | More flexible | More brittle |
| | 'CIFZ0022' | 'Yolindsay Coral' (U.S. Plant Pat. No. 21,210) |
| Flowering response (blackcloth): | Similar | Similar |
| Flowering response (natural): | Slower | 1 week faster |
| Plant size: | Larger | Smaller |
| Flower color: | Coral | Lavender |
| Flower type: | Spider form | (Typical) decorative |

Plant:

*Form, growth and habit*.—Herbaceous garden-type, stems upright and outwardly spreading, freely branching, strong and moderately vigorous growth habit.

*Plant height* (*above soil*).—20-23 cm.

*Plant height* (*inflorescence included*).—27-30 cm.

*Plant width*.—43-58 cm.

Roots:

*Number of days to initiate roots*.—About 4 days at about 22 degrees C.

*Number of days to produce a rooted cutting*.—14-16 days at 22 degrees C.

*Type*.—Fine, fibrous, free branching.

*Color*.—RHS N155B but whiter.

Foliage:

*Arrangement*.—Alternate.

*Immature leaf, color upper surface*.—RHS 137A.

*Immature leaf, color lower surface*.—RHS 137C.

*Mature leaf, color, upper surface*.—RHS 137A.

*Mature leaf, color lower surface*.—RHS 137C.

*Length*.—6.8-7.3 cm.

*Width*.—5.0-5.5 cm.

*Shape*.—Ovate, with distinct lobes.

*Base shape*.—Attenuate an truncate.

*Apex shape*.—Acute.

*Margin*.—5-lobed (palmate), edge serrate.

*Texture, upper surface*.—Bifid hairs.

*Texture, lower surface*.—Bifid hairs.

*Color of veins, upper surface*.—RHS 147B.

*Color of veins, lower surface*.—RHS 147B.

*Pattern of veining*.—Palmate.

*Petiole color*.—RHS 147B.

*Petiole length*.—1.3-1.6 cm.

*Diameter*.—2.0-2.5 cm.

*Texture*.—Covered with bifid hairs.

Stem:

*Quantity of main branches per plant*.—6 to 8.

*Color of stem*.—RHS 147B.

*Length of stem*.—16-18 cm.

*Diameter*.—0.5 cm.

*Length of internodes*.—0.5-1.5 cm.

*Texture*.—Bifid hairs.

*Color of peduncle*.—RHS 147B.

*Length of peduncle*.—3 to 6 cm.

*Peduncle diameter*.—0.2 cm.

*Texture*.—Bifid hairs.

Inflorescence:

*Type*.—Compositae, solitary, decorative-type inflorescences borne terminally above foliage, spoon tipped ray florets arranged acropetally on a capitulum giving a spider flower form.

*Quantity of short days to flowering* (*response time*).—Approximately six weeks.

*Natural season flowering*.—Early October.

*Quantity of inflorescences per plant*.—100-120 (roughly).

*Lastingness of individual blooms on the plant*.—About five weeks from first color.

*Fragrance*.—Slightly spicy.

Bud (when showing color):

*Color*.—Near RHS N185C, soon turning RHS 187D or 187C at the top.

*Length*.—0.7-1.0 cm.

*Width*.—1.3-1.6 cm.

*Shape*.—Oblate (almost globular).

Immature inflorescence:

*Diameter*.—5.0-6.5 cm.

*Color of ray florets, upper surface*.—RHS 186D.

*Color of ray florets, lower surface*.—Close to RHS 186D.

Mature inflorescence:

*Diameter*.—6.4-6.9 cm.

*Depth*.—2.5-2.8 cm.

*Total diameter of disc*.—No disc present.

*Receptacle color*.—RHS 137A (deep green).

*Receptacle height*.—0.4-0.5 cm.

*Receptacle diameter*.—0.4 cm.

Ray florets:

*Average quantity of florets*.—Between 160 and 170 in several whorls.

*Color of florets, upper surface* (*abaxial*).—Lighter than 186D or 70D.

*Color inner surface* (*adaxial*).—RHS 186B to 186C.

*Length*.—3.6-4.0 cm.

*Width/diameter*.—0.5-0.6 cm; 0.3 cm for the tube at the base.

*Shape*.—Predominately spatulate, some quilled.

*Apex shape*.—Mostly obtuse.

*Base shape*.—Tube.

*Margin*.—Entire, small incisions may occur at the tip.

*Texture, upper surface*.—Papillate.

*Lower surface*.—Papillate.

*Disc florets*.—None present.

Phyllaries:

*Quantity.*—20-25.

*Color, upper surface*.—RHS 137A.

*Color, lower surface*.—RHS 137A.

*Length*.—In 2 different sizes: 0.74 or 1.1 cm.

*Width.*—0.2-0.3 cm.

*Shape*.—Lanceolate.

*Apex shape*.—Acute.

*Base*.—Fused.

*Margins*.—Entire.

*Texture, upper surface*.—Glabrous.

*Texture, lower surface*.—Bifid hairs.

Reproductive organs:

*Pistil*.—One.

*Length.*—0.3-0.5 cm.

*Style color*.—RHS 150B.

*Style length.*—0.2-0.3 cm.

*Stigma color*.—RHS 13B.

*Stigma shape*.—Bi-parted.

*Ovary color*.—RHS 145C.

*Ovary length.*—0.15 cm.

*Ovary width.*—0.1 cm.

*Stamens*.—None, as they are usually present in disc florets only, which are not developed.

Fertility/seed set: Has not been determined to date.

Disease/pest resistance: Has not been determined to date.

What is claimed is:

1. A new and distinct variety of *Chrysanthemum* plant named 'CIFZ0022' substantially as illustrated and described herein.

* * * * *